US00PP12105P2

(12) United States Plant Patent
Miyazaki

(10) Patent No.: US PP12,105 P2
(45) Date of Patent: Sep. 25, 2001

(54) TORENIA PLANT NAMED 'SUNRENILAPIHO'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/226,151

(22) Filed: Jan. 7, 1999

(30) Foreign Application Priority Data

Jul. 22, 1998 (JP) ..... 11098

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 10,118 * 11/1997 Miyazaki et al. ..... Plt./68.1
P.P. 10,119 * 11/1997 Nagase ..... Plt./68.1
P.P. 10,120 * 11/1997 Nagase ..... Plt./68.1
P.P. 10,843 3/1999 Tamura et al. ..... Plt./68.1

* cited by examiner

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

Disclosed herein is a torenia plant named 'Sunrenilapiho' which forms in profusion attractive globose bicolored flowers that are white and reddish-purple. The duration of flowering is long and extends from June to November in the southern Kanto area of Japan. A medium branching propensity is displayed. The growth habit is semi-erect with stems that extend downward pliantly when grown in a hanging pot. Good resistance to heat and diseases is exhibited.

2 Drawing Sheets

BACKGROUND OF THE VARIETY

The present invention relates to a new and distinct variety of *Torenia fournieri*×*Torenia concolor* plant that was obtained as a mutation of the 'Sunrenipiho' variety (U.S. Plant Pat. No. 10,118).

The torenia is a very popular plant and is used for flower bedding and potting in the summer season. There are only a few varieties of the torenia plant which have a semi-erect growth habit, and a high resistance to heat and diseases.

Accordingly, this invention was aimed at providing a new torenia variety that forms a great profusion of flowers having bi-colored white and vivid reddish-purple petals, a semi-erect growth habit, and a good resistance to heat and diseases.

The new variety of torenia plant was discovered as a spontaneous branch mutation of the 'Sunrenipiho' variety during March 1996 at the Oumi Research Center of SUNTORY Ltd., located at 863-1, Aza-Iketani, Omori-cho, Yokaichi-shi, Shiga-ken, Japan. The mutant torenia plant was propagated by the use of cuttings beginning in March, 1996 and has been grown in potted plant and bedding trials beginning in April, 1997. The botanical characteristics of the plant were examined, using a similar variety, 'Panda Rose' and the parent variety, 'Sunrenipiho', for comparison. As a result, it was concluded that this new torenia plant is distinguishable from any other variety whose existence is known to us and is uniform and stable in its characteristics following asexual reproduction at such location by the use of cuttings. This new variety of torenia plant has been named 'Sunrenilapiho'.

In the following description, the color-coding is in accordance with the R.H.S. Colour Chart of The Royal Horticultural Society, London, England. The color chart of The Japan Color Standard for Horticultural Plants (J.H.S. Color Chart) is also added for reference in some instances.

The parent variety 'Sunrenipiho' was a mutant of the 'Sunrenibu' variety (U.S. Plant Pat. No. 10,119) obtained from crossing 'Clown Mix' (♀) (non-patented in the United States) and 'Con Color' (♂) (non-patented in the United States). The botanical characteristics of such parent plants are summarized hereafter for comparative purposes when grown in Japan.

BOTANICAL DESCRIPTION OF THE 'Clown Mix' VARIETY

Plant:
- *Growth habit.*—Erect.
- *Plant height.*—20 to 30 cm.
- *Plant width.*—30 to 50 cm.

Stem:
- *Diameter.*—3.0 mm.
- *Anthocyanin pigmentation.*—Present.
- *Branching.*—Slight.
- *Pubescence.*—Sparse.
- *Length of internode.*—1 to 3 cm.

Leaf:
- *Phyllotaxis.*—Opposite.
- *Shape of blade.*—Serrate.
- *Length.*—2.0 to 4.0 cm.
- *Width.*—2.0 to 3.0 cm.
- *Depth of incision.*—Deep.
- *Color.*—Moderate olive green (RHS 137A, JHS 3508).
- *Pubescence of upper side.*—Sparse.

Flower:
- *Facing direction.*—Lateral.
- *Diameter.*—2.0 to 3.0 cm.
- *Length.*—20 to 30 mm.

*Color of floral tube.*—Purplish white (RHS 62D, JHS 8001).
*Color of petal.*—Single color; purplish white (RHS 62D, JHS 8001).
*Yellow eye color.*—Vivid yellow (RHS 17C, JHS 2507).
*Calyx.*—1.5 to 2.0 cm in length.
*Anthocyanin pigmentation of calyx limb.*—Present.
*Peduncle.*—1.5 to 2.0 mm in thickness; and 1.5 to 2.0 cm in length.
*Reproductive organs.*—1 pistil and 4 stamens.
*Anther color.*—White.
*Flowering duration.*—Medium.

Physiological and ecological characteristics: Low resistance to diseases and pests, high tolerance to heat and low tolerance to cold.

BOTANICAL DESCRIPTION OF THE 'Con Color' VARIETY

Plant:
*Growth habit.*—Decumbent.
*Plant height.*—10 to 15 cm.
*Plant width.*—50 to 70 cm.

Stem:
*Diameter.*—1.5 mm.
*Anthocyanin pigmentation.*—Present.
*Branching.*—Substantial.
*Pubescence.*—Sparse.
*Length of internode.*—4 to 6 cm.

Leaf:
*Phyllotaxis.*—Opposite.
*Shape of blade.*—Crenate.
*Length.*—1.0 to 2.0 cm.
*Width.*—1.0 to 2.0 cm.
*Depth of incision.*—Medium.
*Color* (*upper side*).—Moderate olive green (RHS 137A, JHS 3508).
*Pubescence of upper side.*—Sparse.

Flower:
*Facing direction.*—Lateral.
*Diameter.*—20 to 30 mm.
*Length.*—20 to 30 mm.
*Color of floral tube.*—Moderate Purple (RHS 83B, JHS 8613).
*Color of petal.*—Single color; deep purple (RHS 89C, JHS 8311).
*Yellow eye color.*—Absent.
*Calyx.*—1.5 to 2.0 cm in length.
*Anthocyanin pigmentation of calyx limb.*—Present.
*Peduncle.*—1.5 to 2.0 mm in thickness; and 3.0 to 5.0 cm in length.
*Reproductive organs.*—1 pistil and 4 stamens.
*Anther color.*—White.
*Physiological and ecological characteristics.*—High resistance to diseases and pests, high tolerance to heat, and low tolerance of cold.

BOTANICAL DESCRIPTION OF THE 'Sunrenibu' VARIETY

Plant:
*Growth habit.*—Semi-erect. The stems extend downward pliantly when potted in a hanging pot. The plant shape does not change throughout the blooming period.
*Plant height.*—15 to 20 cm.
*Plant width.*—50 to 70 cm. The stems commonly extend to a length of approximately 70 cm from the base.
*Growth.*—Medium branching with a great profusion of blooms with the entire plant remaining in bloom for a considerable period of time.
*Blooming period.*—June to November in the southern Kanto area, Japan.

Stem:
*Diameter.*—2.0 mm.
*Anthocyanin pigmentation.*—Present.
*Branching.*—Moderate.
*Pubescence.*—Sparse.
*Length of internode.*—4 to 6 cm.

Leaf:
*Phyllotaxis.*—Opposite.
*Shape of blade.*—Serrate.
*Length.*—1.0 to 3.0 cm.
*Width.*—1.0 to 2.0 cm.
*Depth of incision.*—Medium.
*Color.* (*upper side*).—Medium olive green (RHS 137A, JHS 3508).
*Pubescence of upper side.*—Sparse.

Flower:
*Facing direction.*—Lateral.
*Diameter.*—20 to 30 mm.
*Length.*—20 to 30 mm.
*Color of floral tube.*—Light Purple (RHS 92B, JHS 8303).
*Color of petal.*—Solid color; Vivid Purple (RHS 89B, JHS 8607).
*Yellow eye color.*—Absent.
*Calyx.*—1.5 to 2.0 cm in length.
*Anthocyanin pigmentation of calyx limb.*—Present.
*Peduncle.*—1.5 to 2.0 mm in thickness; and 2.0 to 3.0 cm in length.
*Reproductive organs.*—1 pistil and 4 stamens.
*Anther color.*—White.

Physiological and ecological characteristics: Moderate resistance to diseases and pests, high tolerance to heat, and low tolerance to cold. Can be grown in the shade.

BOTANICAL DESCRIPTION OF THE 'Sunrenipiho' VARIETY

Plant:
*Growth habit.*—Semi-erect. The stems extend downward pliantly when potted in a hanging pot. The plant shape does not change throughout the blooming period.
*Plant height.*—15 to 20 cm.
*Plant width.*—50 to 60 cm. The stems commonly extend to length of approximately 60 cm from the base.
*Growth.*—Medium branching with a great profusion of blooms with the entire plant remaining in bloom for a considerable period of time.
*Blooming period.*—June to November in the southern Kanto area, Japan.

Stem:
*Diameter.*—2.0 mm.
*Anthocyanin pigmentation.*—Present and dark.
*Branching.*—Medium.
*Pubescence.*—Sparse.
*Length of internode.*—5 cm.

Leaf:
*Phyllotaxis.*—Opposite.

*Shape of blade.*—Lanceolate.
*Length.*—3.0 cm.
*Width.*—2.0 cm.
*Depth of incision.*—Medium.
*Color.(upper side).*—Moderate olive green (RHS 137A, JHS 3508).
*Pubescence of upper side.*—Sparse.
*Thickness of petiole.*—Medium.
*Length of petiole.*—Short.

Flower:
*Inflorescence peduncles.*—Axillary.
*Flower form.*—Globose.
*Flower diameter.*—Medium. (28 mm).
*Flower width.*—Medium. (24 mm).
*Length of floral tube.*—Medium. (30 mm).
*Color of floral tube.*—Strong reddish purple (RHS 78B, JHS 8905).
*Color of upper bilabiate petal.*—Yellowish white (RHS 155D, JHS -01).
*Color of intermediate bilabiate petal.*—Strong reddish-purple (RHS 78B, JHS 8905).
*Color of lowest bilabiate petal.*—Yellowish-white. (RHS 78B).
*Vertical line on the petal.*—Absent.
*Wave of upper bilabiate petal.*—Substantial margin undulation.
*Calyx shape.*—Shallowly five-lobed.
*Calyx length.*—Short to medium. (approximately 15 mm).
*Anthocyanin pigmentation of calyx limb.*—Moderate.
*Anthocyanin pigmentation of anther.*—Sparse.
*Anther spur.*—Absent.
*Anther color.*—White.
*Peduncle thickness.*—Medium (approximately 1.5 mm).
*Peduncle length.*—Medium. (approximately 25 mm).
*Reproductive organs.*—1 pistil and 4 stamens.

Physiological and ecological characteristics: Medium resistance to disease and pests, high tolerance to heat, and low tolerance to cold.

BOTANICAL DESCRIPTION OF THE 'Panda Rose' VARIETY

Plant:
*Growth habit.*—Erect.
*Plant height.*—26 cm.

Stem:
*Diameter.*—3.2 mm.
*Anthocyanin pigmentation.*—Sparse.
*Branching.*—Medium.
*Pubescence.*—Moderate.
*Length of internode.*—6.4 cm.

Leaf:
*Phyllotaxis.*—Opposite.
*Shape of blade.*—Lanceolate.
*Length.*—7.2 cm.
*Width.*—3.8 cm.
*Depth of incision.*—Medium.
*Pubescence of upper side.*—Moderate.
*Thickness of petiole.*—Relatively thick.
*Length of petiole.*—Long.

Flower:
*Inflorescence peduncles.*—Terminal.
*Flower form.*—Ellipsoidal.
*Flower length.*—Medium (approximately 26 mm).
*Flower width.*—Medium (approximately 19 mm).
*Length of floral tube.*—Medium (32 mm).
*Color of floral tube.*—Yellowish-white (RHS 155D, JHS 2901).
*Color of upper bilabiate petals.*—Yellowish-white (RHS 155D, JHS 2901).
*Color of intermediate bilabiate petals).*—Vivid purplish-red (RHS 67B, JHS 9507).
*Color of lowest bilabiate petal.*—Vivid purplish-red (RHS 67B, JHS 9507).
*Color pattern of bilabiate petal.*—Bi-colored.
*Yellow blotches on the petals.*—Present.
*Vertical line on the petals.*—Absent.
*Wave of upper bilabiate petal.*—Substantial margin undulation.
*Calyx shape.*—Shallowly lobed.
*Calyx length.*—Medium (approximately 17 mm).
*Anthocyanin pigmentation of calyx limb.*—Slight.
*Anthocyanin pigmentation of anther.*—Slight.
*Anther spur.*—Absent.
*Peduncle thickness.*—Medium (approximately 1.2 mm).
*Peduncle length.*—Medium (approximately 24 mm).
*Reproductive organs.*—1 pistil and 4 stamens.

Physiological and ecological characteristics: Moderate resistance to heat, cold, diseases and pests.

SUMMARY OF THE NEW VARIETY

The new variety of torenia plant named 'Sunrenilapiho' has a semi-erect growth habit, and bi-colored white and vivid reddish-purple flower petals without yellow blotches. The new variety has medium branching, and forms great profusion of blooms with the entire plant remaining in bloom for a considerable period of time.

BRIEF DESCRIPTION OF THE PHOTOGRAPHS

DETAILED DESCRIPTION OF THE NEW VARIETY

Figure 1:
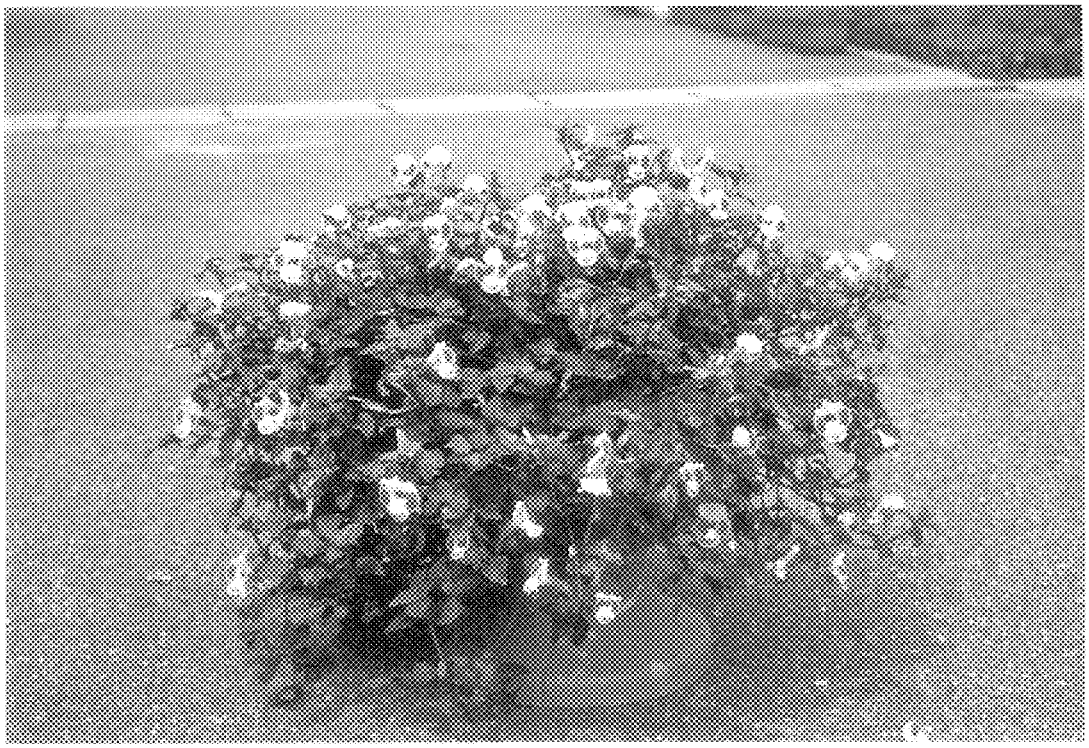
FIG. 1 is a photograph giving a partial view of the new variety of torenia plant of the present invention growing in a flower pot.
Figure 2:
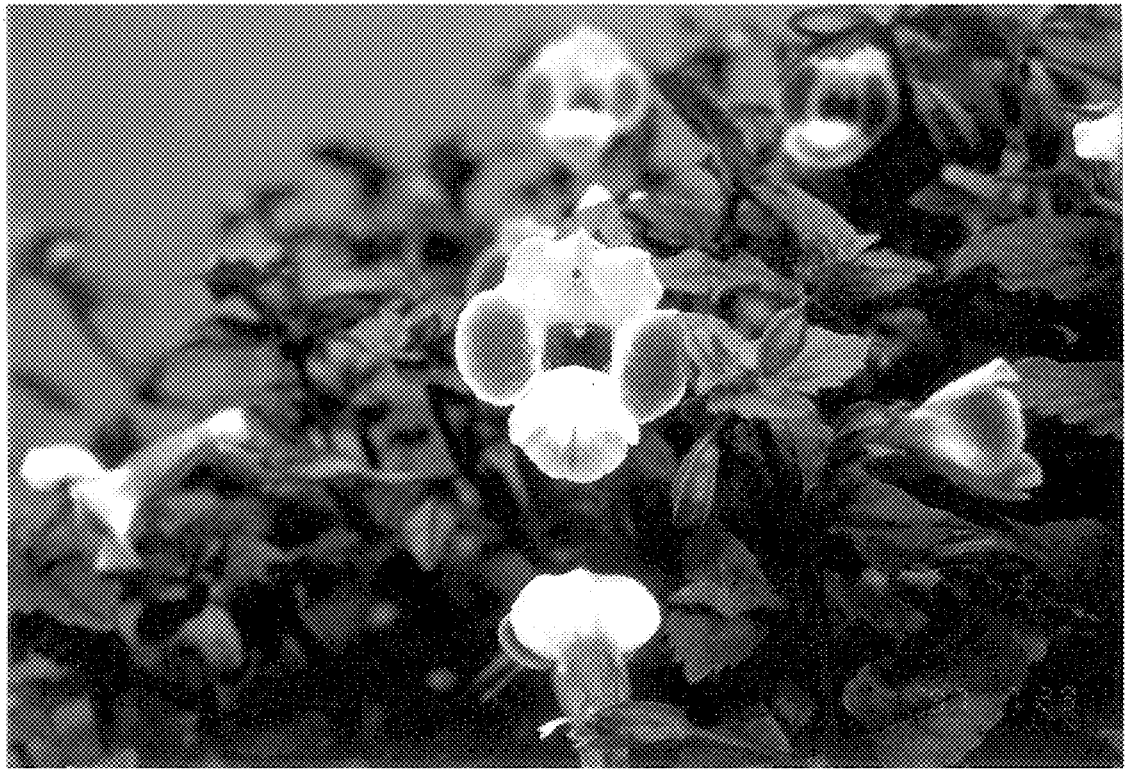
FIG. 2 is a photograph of flowers and foliage of the new variety of torenia plant of the present invention.

The botanical characteristics of the new and distinct variety of torenia plant 'Sunrenilapiho' are set forth below. Young nursery plants were planted in the field during April and were observed during July when growing in Japan.

Plant:
*Growth habit.*—Semi-erect. The stems extend downward pliantly when potted in a hanging pot.
*Plant height.*—15 cm.
*Growth.*—Medium branching with a great profusion of blooms; the entire plant remains in bloom for a considerable this period of time. At the peak of blooming a single plant will have approximately 50 blooms.
*Blooming period.*—June to November in the southern Kanto area, Japan. The plant shape does not change throughout this blooming period.

Stem:
*Diameter.*—Approximately 2.7 mm.
*Anthocyanin pigmentation.*—Present, and dark (RHS 166A).
*Branching.*—Medium.

*Pubescence.*—Few.
*Length of internode.*—5.5 cm.
*Color.*—Moderate yellow green (RHS 143C, JHS 3709).

Leaf:
*Phyllotaxis.*—Opposite.
*Shape of blade.*—Lanceolate.
*Length.*—3.8 cm.
*Width.*—3.2 cm.
*Margin.*—Dentate.
*Color. (upper side).*—RHS 138A when immature and RHS 137A when mature.
*Color. (reverse side).*—RHS 138B when immature and RHS 137C when mature.
*Pubescence on upper side.*—Sparse.
*Thickness of petiole.*—Approximately 1.8 mm.
*Length of petiole.*—Approximately 8.0 mm.

Flower:
*Inflorescence peduncles.*—Axillary.
*Flower form.*—Globose.
*Flower length.*—Medium to Long (approximately 35 mm).
*Flower diameter.*—Long (approximately 33 mm) across the flower face parallel to the horizontal plane.
*Color of floral tube.*—Vivid reddish-purple (RHS 80A, JHS 8906).
*Color of upper bilabiate petals.*—Pale purplish-white (RHS 76D) on the upper surface and on the lower surface.
*Color of intermediate bilabiate petals.*—RHS 80A in the center with white margins on the upper surface and RHS 82A with white margins on the lower surface.
*Color of lowest bilabiate petals.*—RHS 78B towards the base except for a white margin and white towards the tip on the upper surface and the lower surface.
*Color pattern of bilabiate petal.*—Bi-colored.
*Yellow blotches on the petals.*—Absent.
*Vertical line on the petals.*—Absent.
*Wave of upper bilabiate petal.*—Substantial margin undulation.
*Calyx shape.*—Deeply lobed with a depth of approximately 10 mm.
*Calyx length.*—Medium. (approximately 19 mm).
*Anthocyanin pigmentation of calyx.*—Present towards the tip.
*Anthocyanin pigmentation of anther.*—None present.
*Anther spur.*—Absent.
*Anther color.*—White.
*Peduncle thickness.*—Medium (approximately 1.5 mm).
*Peduncle length.*—Medium (22 mm).
*Flower presentation.*—Raceme.
*Flower number.*—Commonly 1 to 2 per node.
*Reproductive organs.*—1 pistil and 4 stamens.
*Flowering time.*—Late, early summer to mid-autumn.

Physiological and ecological characteristics: Moderate resistance to heat, cold, diseases and pests. Severe frost may be harmful to the plant. The resistance to Powdery Mildew is moderate.

This new 'Sunrenilapiho' variety is most suitable for flower bedding and potting, and is particularly well suited for growing in hanging pots and in planters.

I claim:

1. A new and distinct variety of torenia plant named 'Sunrenilapiho' substantially as herein illustrated and described, that displays:

(a) A semi-erect growth habit with stems that extend downward pliantly when grown in a hanging pot,
(b) A medium branching propensity, and
(c) Forms attractive bicolored white and reddish-purple flowers in profusion from June to November in the southern Kanto area of Japan;

substantially as herein shown and described.

* * * * *